(12) United States Patent
Kabra

(10) Patent No.: US 9,421,265 B2
(45) Date of Patent: *Aug. 23, 2016

(54) AQUEOUS PHARMACEUTICAL COMPOSITIONS CONTAINING BORATE-POLYOL COMPLEXES

(71) Applicant: Alcon Research, Ltd., Fort Worth, TX (US)

(72) Inventor: Bhagwati P. Kabra, Euless, TX (US)

(73) Assignee: Alcon Research, LTD., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,617

(22) Filed: Apr. 20, 2015

(65) Prior Publication Data

US 2015/0224196 A1   Aug. 13, 2015

Related U.S. Application Data

(63) Continuation of application No. 12/817,561, filed on Jun. 17, 2010, now Pat. No. 9,044,484.

(60) Provisional application No. 61/218,472, filed on Jun. 19, 2009.

(51) Int. Cl.

| | | |
|---|---|---|
| A61K 47/18 | (2006.01) | |
| A61K 31/498 | (2006.01) | |
| A61P 27/02 | (2006.01) | |
| A61K 9/00 | (2006.01) | |
| A61K 31/542 | (2006.01) | |
| A61K 47/10 | (2006.01) | |
| A61K 47/26 | (2006.01) | |
| A61K 47/32 | (2006.01) | |
| A61K 47/02 | (2006.01) | |
| A61K 47/36 | (2006.01) | |

(52) U.S. Cl.
CPC .............. *A61K 47/186* (2013.01); *A61K 9/0048* (2013.01); *A61K 31/498* (2013.01); *A61K 31/542* (2013.01); *A61K 47/02* (2013.01); *A61K 47/10* (2013.01); *A61K 47/26* (2013.01); *A61K 47/32* (2013.01); *A61K 47/36* (2013.01)

(58) Field of Classification Search
None
See application file for complete search history.

(56) References Cited

U.S. PATENT DOCUMENTS

| | | |
|---|---|---|
| 3,931,319 A | 1/1976 | Green et al. |
| 4,027,020 A | 5/1977 | Green et al. |
| 4,407,791 A | 10/1983 | Stark |
| 4,522,806 A | 6/1985 | Muhlemann et al. |
| 4,525,346 A | 6/1985 | Stark |
| 4,836,986 A | 6/1989 | Ogunbiyi et al. |
| 5,037,647 A | 8/1991 | Chowhan et al. |
| 5,130,298 A | 7/1992 | Cini et al. |
| 5,221,664 A | 6/1993 | Berkowitz et al. |
| 5,300,287 A | 4/1994 | Park |
| 5,320,843 A | 6/1994 | Raheja et al. |
| 5,352,708 A | 10/1994 | Woodward et al. |
| 5,424,078 A | 6/1995 | Dziabo et al. |
| 5,458,873 A | 10/1995 | Kawashima et al. |
| 5,460,834 A | 10/1995 | Bhagat |
| 5,505,953 A | 4/1996 | Chowhan |
| 5,597,559 A | 1/1997 | Olejnik et al. |
| 5,603,929 A | 2/1997 | Desai et al. |
| 5,607,698 A | 3/1997 | Martin et al. |
| 5,631,287 A | 5/1997 | Schneider |
| 5,653,972 A | 8/1997 | Desai et al. |
| 5,683,993 A | 11/1997 | Tsao |
| 5,725,887 A | 3/1998 | Martin et al. |
| 5,736,165 A | 4/1998 | Ripley et al. |
| 5,741,817 A | 4/1998 | Chowhan et al. |
| 5,811,466 A | 9/1998 | Chowhan et al. |
| 5,817,277 A | 10/1998 | Mowrey-McKee et al. |
| 5,820,822 A | 10/1998 | Kross |
| 5,849,792 A | 12/1998 | Schneider |
| 5,858,346 A | 1/1999 | Vehige et al. |
| 5,858,996 A | 1/1999 | Tsao |
| 6,011,062 A | 1/2000 | Schneider et al. |
| 6,017,861 A | 1/2000 | Fujiwara et al. |
| 6,024,954 A | 2/2000 | Park et al. |
| 6,034,043 A | 3/2000 | Fujiwara et al. |
| 6,071,904 A | 6/2000 | Ali et al. |
| 6,121,315 A | 9/2000 | Nair et al. |
| 6,143,799 A | 11/2000 | Chowhan et al. |
| 6,316,441 B1 | 11/2001 | Dean et al. |
| 6,319,464 B1 | 11/2001 | Asgharian |
| 6,348,190 B1 | 2/2002 | Illes et al. |

(Continued)

FOREIGN PATENT DOCUMENTS

| | | |
|---|---|---|
| EP | 0 462 460 | 10/1996 |
| EP | 2722035 A1 | 4/2014 |

(Continued)

OTHER PUBLICATIONS

Burger, Artur er al., "Hunnius Pharmazeutisches Wörterbuch", Walter de Gruyter & Co., 1986, p. 827, Ed. 6, Berlin.
Collins English Dictionary, HarperCollins Publishers, 2007, p. 1741.
European Patent Office, Communication of a Notice of Opposition, Opponent: Teva Pharmaceuticals Industries Ltd., Application No. 10727317.9, Patent No. 2442790, Jan. 12, 2015, 33 pgs.
European Patent Office, Communication of a Notice of Opposition, Opponent: Generics [UK] Limited (trading as Mylan), Application No. 10727317.9, Patent No. 2442790, Jan. 14, 2015, 50 pgs.
Guang, Tang, "benzalkonium chloride", Practical Manual of Ophthalmology and Otorhinolaryngology Medicines, China Medical Science Press, Jan. 2001, pp. 108-109.

(Continued)

*Primary Examiner* — Theodore R West
(74) *Attorney, Agent, or Firm* — Scott A. Chapple

(57) ABSTRACT

The present invention is directed to the provision of multi-dose, ophthalmic compositions. The compositions possess sufficient antimicrobial activity to satisfy USP preservative efficacy requirements, as well as similar preservative standards (e.g., EP and JP). The compositions include at two different polyols in conjunction with borate and a low concentration of benzalkonium chloride.

20 Claims, No Drawings

(56) References Cited

U.S. PATENT DOCUMENTS

| | | | |
|---|---|---|---|
| 6,365,636 | B1 | 4/2002 | Chowhan et al. |
| 6,482,799 | B1 | 11/2002 | Tuśe et al. |
| 6,492,361 | B1 | 12/2002 | Muller et al. |
| 6,503,497 | B2 | 1/2003 | Chowhan et al. |
| 6,583,124 | B2 | 6/2003 | Asgharian |
| 6,743,439 | B1 | 6/2004 | Castillo et al. |
| 6,849,253 | B2 | 2/2005 | Chowhan et al. |
| 7,074,827 | B2 | 7/2006 | Ueno |
| 7,445,771 | B2 | 11/2008 | Dassanayake et al. |
| 9,044,484 | B2 * | 6/2015 | Kabra ............... A61K 9/0048 |
| 2002/0122831 | A1 | 9/2002 | Mowrey-McKee et al. |
| 2002/0123482 | A1 | 9/2002 | Chowhan et al. |
| 2004/0127372 | A1 | 7/2004 | Ketelson et al. |
| 2005/0129771 | A1 | 6/2005 | Asgharian |
| 2005/0214382 | A1 | 9/2005 | Xia et al. |
| 2005/0239900 | A1 | 10/2005 | Asgharian |
| 2006/0205725 | A1 | 9/2006 | Ueno |
| 2007/0212420 | A1 | 9/2007 | Xia et al. |
| 2007/0287749 | A1 | 12/2007 | Sawa et al. |
| 2007/0293558 | A1 | 12/2007 | Gao et al. |
| 2007/0297990 | A1 | 12/2007 | Shah et al. |
| 2008/0075790 | A1 | 3/2008 | Kabra et al. |
| 2008/0093247 | A1 | 4/2008 | Han et al. |
| 2008/0095863 | A1 | 4/2008 | Kabra |
| 2009/0232763 | A1 | 9/2009 | Kabra et al. |
| 2010/0227003 | A1 | 9/2010 | Shah et al. |

FOREIGN PATENT DOCUMENTS

| | | |
|---|---|---|
| JP | 10130156 | 5/1998 |
| JP | 2002265357 | 9/2002 |
| JP | 2003-104870 | 4/2003 |
| WO | 91/09523 | 7/1991 |
| WO | 93/21903 | 11/1993 |
| WO | 95/13050 | 5/1995 |
| WO | 98/10773 | 3/1998 |
| WO | 98/52579 | 11/1998 |
| WO | 2005060953 A1 | 7/2005 |
| WO | 2005/097067 | 10/2005 |
| WO | 2007/106723 | 9/2007 |
| WO | 2008/002118 | 1/2008 |
| WO | 2008/036847 | 3/2008 |
| WO | 2008042619 A2 | 4/2008 |
| WO | 2008131013 A1 | 10/2008 |
| WO | 2009/117242 | 9/2009 |
| WO | 2009/117316 | 9/2009 |
| WO | 2010124225 A1 | 10/2010 |

OTHER PUBLICATIONS

Borokhov et al., "New Biocides Development Chapter 20: Antimicrobial Properties of Boron Derivatives," American Chemical Society, Sep. 7, 2007, pp. 412-435.
Lambert et al., The synergistic effect of EDTA/antimicrobial combinations on Pseudomonas aeruginosa, Journal of Applied Microbiology, 2004, pp. 244-253, vol. 96.
Safety Data Sheet, U.S. Pharmacopeial Convention, Issue date: Dec. 6, 2006, Revision date: Feb. 28, 2014, pp. 1-6.
U.S. Appl. No. 61/037,117, filed Mar. 17, 2008.
Hoffman et al.; "Pre-clinical in vitro testing of an artificial tear formulation with a novel preservative system", poster presentation at the annual meeting of the Association for Research in Vision and Ophthalmology (ARVO), Ft. Lauderdale, FL, Apr. 30, 2006.
Systane Free promotional document (minimal-blur) published on or about Jan. 1, 2006.
Bhagav et al.; "Development and validation of stability indicating UV spectrophotometric method for the estimation of brimonidine tartrate in pure form, formulations and preformulation studies"; Scholars Research Library; Der Pharmacia Lettre; vol. 2. No. 3; pp. 106-122 (2010); www.scholarsresearchlibrary.com (http://scholarsresearchlibrary.com/archive.html).
Rase et al., "Effect and safety of Benzalkonium chloride in an ophthalmic solution containing Ofloxacin", Der Chemica Sinica, 2011, 278-282, 2(2).
Ammar et al., "Effects of Benzalkonium Chloride-preserved, Polyquad-Preserved, and sofZia-Preserved Topical Glaucoma Medications on Human Ocular Epithelial Cells", Ad. Ther., 2010, 27(11).
Ayaki et al., "Toxicity of antiglaucoma drugs with and without benzalkonium chloride to cultured human corneal endothelia cells", Clinical Ophthlamology, 2010, 4, 1217-1222.
Freeman et al., "Preservatives in topical ophthalmic medications: historical and clinical perspectives", Expert Rev Ophthalmol, 2009, 4(1), 59-64.
Grahn et al., Apr. 2001, "Zinc and the eye", Journal of the American College of Nutrition, vol. 20, No. 2, 106-118.
Guttman, "Liquid gel therapy broadens role of dry eye product line", Ophthalnnologytimes.com, 2006, pp. 33-34 and copyright notice.
Illustration of packaging for Systane® free.
Kabara et al., 1997, Preservative-Free and Self-Preserving Cosmetics and Drugs—Principles and Practice, Chapter 1, pp. 1-14, Marcel Dekker, Inc.
McCarthy, 1985, "Metal Ions as Microbial Inhibitors", Cosmetic & Toiletries, 100:69-72.
McCarthy et al., 1989, "The Effect of Zinc Ions on the Antimicrobial Activity of Selected Preservatives", Journal of Pharmacy and Pharmacology, vol. 41, 114P.
Zeelie et al., 1992, "The Effects of Selected Metal Salts on the Microbial Activities of Agents used in the Pharmaceutical and Related Industries", Metal Compounds in Environment and Life, 4:193-200.
Zeelie et al., 1998, "Effects of copper and zinc ions on the germicidal properties of two popular pharmaceutical antiseptic agents cetylpyridinium chloride and povidone-iodine", Analyst, 123:503-507.
Feldman et al., Additivity Study Group, 2007, "Comparison of the Ocular Hypotensive Efficacy of Adjunctive Brimonidine 0.15% or Brinzolamide 1% in Combination with Travoprost 0.004%", Ophthalmology, vol. 114(7), 1248-1254.
PCT International Search Report for corresponding PCT/US2010/038979 with mailing date Aug. 20, 2010.
PCT International Written Opinion for corresponding PCT/US2010/038979 with mailing date Aug. 20, 2010.
Houlsby R D et al., 1986, "Antimicrobial activity of borate-buffered solutions", Antimicrobial Agents and Chemotherapy, American Society for Microbiology, vol. 29, No. 5, 803-806.
"Lubrizol", Pharmaceutical Bulletin 22, May 31, 2011, pp. 1-5.

* cited by examiner

AQUEOUS PHARMACEUTICAL COMPOSITIONS CONTAINING BORATE-POLYOL COMPLEXES

CROSS REFERENCE TO RELATED APPLICATION

This application is a continuation application of U.S. Utility patent application Ser. No. 12/817,561 filed Jun. 17, 2010 (now allowed), which claims priority under 35 U.S.C. §119 to U.S. Provisional Patent Application Ser. No. 61/218,472, filed Jun. 19, 2009, the entire contents of which are incorporated herein by reference.

TECHNICAL FIELD OF THE INVENTION

The present invention is related to pharmaceutical compositions that contain borate-polyol complexes for improved preservation of the compositions. More specifically the present invention relates to aqueous pharmaceutical compositions (e.g., multi-dose ophthalmic compositions) containing two or more different polyols in conjunction with borate and a preservative, particularly benzalkonium chloride (BAC).

BACKGROUND OF THE INVENTION

The present invention is directed to pharmaceutical compositions formulated so as to have sufficient antimicrobial activity to satisfy the preservation efficacy requirements of the United States Pharmacopeia ("USP") and analogous guidelines in other countries. The ability to achieve preservation is based on a unique combination of formulation components and particularly the use of two or more different polyols in combination with borate and a preservative, particularly BAC.

Many pharmaceutical compositions are required to be sterile (i.e., substantially free of bacteria, fungi and other pathogenic microorganisms). Examples of such compositions include: solutions and suspensions that are injected into the bodies of humans or other mammals; creams, lotions, solutions or other preparations that are topically applied to wounds, abrasions, burns, rashes, surgical incisions, or other conditions where the skin is not intact; and various types of compositions that are applied either directly to the eye (e.g., artificial tears, irrigating solutions, and drug products), or are applied to devices that will come into contact with the eye (e.g., contact lenses).

The foregoing types of compositions can be manufactured under sterile conditions via procedures that are well known to those skilled in the art. However, once the packaging for a product is opened, such that the composition contained therein is exposed to the atmosphere and other sources of potential microbial contamination (e.g., the hands of a human patient), the sterility of the product may be compromised. Such products are typically utilized multiple times by the patient, and are therefore frequently referred to as being of a "multi-dose" nature.

Due to the frequent, repeated exposure of multi-dose products to the risk of microbial contamination, it is necessary to employ a means for preventing such contamination from occurring. The means employed may be: (i) a chemical agent that prevents the proliferation of microbes in a composition, which is referred to herein as an "antimicrobial preservative"; or (ii) a packaging system that prevents or reduces the risk of microbes reaching a pharmaceutical composition within a container.

Prior multi-dose ophthalmic compositions have generally contained one or more antimicrobial preservatives in order to prevent the proliferation of bacteria, fungi and other microbes. Such compositions may come into contact with the cornea either directly or indirectly. The cornea is particularly sensitive to exogenous chemical agents. Consequently, in order to minimize the potential for harmful effects on the cornea, it is preferable to use anti-microbial preservatives that are relatively non-toxic to the cornea, and to use such preservatives at relatively low concentrations.

Balancing the anti-microbial efficacy and potential toxicological effects of anti-microbial preservatives is sometimes difficult to achieve. More specifically, the concentration of an antimicrobial agent necessary for the preservation of ophthalmic formulations from microbial contamination may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (i.e., antimicrobial preservation). The use of an inadequate level of antimicrobial preservation may create the potential for microbial contamination.

This balance between anti-microbial efficacy and potential toxicological effects of anti-microbial preservatives is additionally complicated by the fact that many anti-microbial preservatives are ineffective when used in conjunction with some pharmaceutical excipients and/or some pharmaceutical therapeutic agents. For example, some preservatives are rendered less effective when used in conjunction with negatively charged therapeutic agents or excipients.

It has been found that BAC is often desirable as a preservative in conjunction with a wide variety of therapeutic agents and pharmaceutical excipients for situations where other preservatives can be ineffective. It has also been found, however, that BAC can rapidly lose its anti-microbial efficacy when its concentration falls below certain threshold levels. This loss of efficacy is quite unfortunate since concentrations of BAC below these threshold levels can exhibit significantly lower toxicological effects. As such, it would be quite desirable to develop a preservative system that can enhance the anti-microbial effects of low concentrations of BAC such that BAC can be used in situations where other preservatives might be ineffective. Such a system would be particularly desirable for ophthalmic compositions.

Ophthalmic compositions are generally formulated as isotonic, buffered solutions. Particularly desirable ophthalmic compositions are those containing borate or borate-polyol complexes. Examples of such compositions are disclosed in U.S. Pat. Nos. 6,503,497; 6,011,062; 6,849,253; 5,603,929; 5,653,972; 5,849,792; and 5,631,287, all of which are incorporated herein by reference for all purposes.

It is generally known that borate-polyol complexes can be used in ophthalmic compositions to enhance anti-microbial activity in the presence of a preservative such as a polymeric quaternary ammonium; see U.S. Pat. Nos. 5,505,953; 5,811,466; 6,143,799; and 6,365,636, all of which are also incorporated herein by reference for all purposes. It has also been shown that increase in amounts of polyol such as sorbitol or mannitol can significantly increase anti-microbial activity even when relatively low amounts of borate are employed. However, mannitol and sorbitol can also affect the resistance to normalization of tear pH after instillation of the compositions in the eye.

Generally, the borate component (e.g., boric acid) of these complexes can provide the ophthalmic composition with significant resistance to normalization of tear pH. It is generally desirable for these ophthalmic compositions to exhibit at least some degree of buffering so that the natural pH of the compositions does not change significantly over time. However, it is also possible for the compositions to exhibit an undesirably high degree of buffering such that, when applied, they can cause tearing of the eye and discomfort to the eye as the eye attempts to maintain its own pH. Thus, it is desirable to minimize the resistance of the compositions to normalization of tear pH after application. The aforementioned polyols, particularly mannitol, sorbitol or both, can significantly enhance the resistance to normalization of tear pH of the borate component. Thus, for the purpose of maintaining desired levels of buffering, it is typically desirable to maintain relatively low concentrations of these polyols in the presence of borate. However, such lower concentrations can limit or lower the anti-microbial activity of the ophthalmic compositions.

In view of the above, it would be particularly desirable to provide an ophthalmic composition, which includes borate-polyol complex formed with lower concentrations of particular polyols and/or borate and includes low concentrations of BAC while exhibiting improved anti-microbial activity and desirable buffering activity.

SUMMARY OF THE INVENTION

The present invention is directed to a multi-dose ophthalmic composition that includes a first polyol, a second polyol, borate and benzalkonium chloride (BAC). The first polyol is selected from mannitol, sorbitol or a combination thereof. The second polyol is selected from propylene glycol, glycerine or a combination thereof. The borate is included in an effective amount and that effective amount is than about 0.5 w/v % of the overall composition. The BAC is used as an anti-microbial preservative and the concentration of BAC in the composition is greater than 0.00001 w/v % but less than 0.0035 w/v %. The composition is preferably aqueous and is typically at least 70 w/v % and more typically at least 90 or 95 w/v % purified water.

DETAILED DESCRIPTION OF THE INVENTION

The present invention is predicated upon the provision of two or more different polyols in the presence of borate and benzalkonium chloride (BAC) for providing a pharmaceutical composition and particularly an ophthalmic composition that exhibits desired anti-microbial activity and/or desired buffering activity. Thus, the ophthalmic composition typically includes a first polyol, a second polyol different from the first polyol, BAC and borate. It is contemplated that the ophthalmic composition can be a contact lens solution (e.g., a contact lens storage or washing solution) or other type of ophthalmic composition. In a preferred embodiment, however, the ophthalmic composition is a single or multi-dose ophthalmic composition containing a therapeutic agent. The composition is typically configured for topical application to the eye (e.g., as drops directly to the eye).

Unless otherwise indicated, percentages provided for the ingredients of the ophthalmic composition of the present invention are weight/volume (w/v) percentages.

As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol.

As utilized herein, the phrase "less than" relative to a specified concentration (e.g., 1 w/v %) means that the specified component (e.g., antimicrobial preservative) is either not present in the composition at all or is present at a concentration less than the specified limit (e.g., 1 w/v %). As utilized herein, the phrase "an effective amount of" means that a specified component is present in the composition in an amount sufficient to have an impact on the therapeutic capability, the buffering capability, the preservative capability and/or the anti-microbial capability of the composition.

The compositions of the present invention typically include the preservative benzalkonium chloride. As used herein, benzalkonium chloride (BAC) shall, unless otherwise specifically stated, mean alkyldimethylbenzylammonium chloride (ADBAC) and all derivatives thereof. Derivatives of ADBAC include compounds where the alkyl group of ADBAC has been shortened or lengthened and/or where one or both of the two methyl groups of ADBAC have been changed to a larger alkyl group.

The composition of the present invention can include other preservatives in addition to BAC. Potential additional preservatives include, without limitation, hydrogen peroxide and polymeric quaternary ammonium compounds. However, it is preferable that the composition be substantially free or entirely free of any preservatives other than BAC.

As used herein, the phrase "substantially free of" as it refers to an ingredient of the ophthalmic composition means that it is contemplated that the ophthalmic solution can be either entirely devoid of that particular ingredient or includes only a nominal amount of that particular ingredient.

BAC is typically in the compositions of the present invention in an amount that is greater than about 0.00001 w/v %, more typically greater than about 0.0003 w/v % and even more typically greater than about 0.0007 w/v % of the ophthalmic composition. Moreover, BAC is generally used in the compositions of the present invention in an amount that is less than about 0.005 w/v %, more typically less than about 0.0035 w/v % and even possibly less than about 0.0025 or even less than about 0.0015 w/v % of the ophthalmic composition.

As suggested previously, the ophthalmic composition will include a combination of two or more polyols with first polyol being different from second polyol. The first polyol is preferably one that significantly enhances the resistance of the borate component to normalization of tear pH upon instillation of the ophthalmic composition in the eye. In contrast, the second polyol is preferably one that does not or only minimally enhances such resistance of the borate component of the ophthalmic composition.

The first polyol can be a single polyol or group of polyols. Each of the polyols of the first polyol is preferably a sugar alcohol that includes an alkyl chain with hydroxyl group (—OH groups) attached to a substantial portion (i.e., greater than 50, 70 or 90 percent or all) of the carbons in the alkyl chain. The alkyl chains of each of the polyols of the first polyol typically include 5 carbons (pentane), 6 carbons (hexane), 7 carbons (heptane) or any combination thereof. Examples of suitable polyols for the first polyol include, without limitation, mannitol ((2R,3R,4R,5R)-hexane-1,2,3, 4,5,6-hexol), sorbitol ((2R,3S,4S,5S)-hexane-1,2,3,4,5,6-hexol), combinations thereof or the like. Another possible suitable polyol for the first polyol is xylitol ((2R,3r,4S)-pentane-1,2,3,4,5-pentaol). In a preferred embodiment, the first polyol is entirely or substantially entirely (i.e., at least 95% by weight) mannitol or sorbitol or both. Of these, it typically preferred that the first polyol be substantially entirely mannitol.

As used herein, the term "substantially entirely", when used to describe what ingredient[s] are part of a component of the ophthalmic composition, means that it is contemplated that the component is formed entirely of one or more particular ingredient[s] or is formed substantially entirely of those one or more particular ingredient[s] with only a nominal amount of the component being formed of other than those one or more particular ingredients.

The first polyol is typically at least about 0.01 w/v %, more typically at least about 0.15 w/v % and even more typically at least about 0.25 w/v % of the ophthalmic composition. The first polyol is also typically less than about 5 w/v %, more typically less than about 1.6 w/v % and even more typically less than about 0.5 w/v % of the ophthalmic composition.

The second polyol can also be a single polyol or group of polyols. Each of the polyols of the second polyol, like the first polyol, is preferably a sugar alcohol that includes an alkyl chain with hydroxyl group (—OH groups) attached to a substantial portion (i.e., greater than 50, 70 or 90 percent or all) of the carbons in the alkyl chain. The alkyl chains of each of the polyols of the second polyol typically include 2 carbons (ethane), 3 carbons (propane) or 4 carbons (butane). Examples of suitable polyols for the second polyol include, without limitation, glycerol (propane-1,2,3-triol), propylene glycol (propane-1,2-diol)1, combinations thereof or the like. In a preferred embodiment, the second polyol is entirely or substantially entirely (i.e., at least 95% by weight) glycerol or propylene glycol or both. Of these, it typically preferred that the second polyol be substantially entirely propylene glycol.

The second polyol is typically at least about 0.015 w/v %, more typically at least about 0.2 w/v % and even more typically at least about 0.3 w/v % of the ophthalmic composition. The first polyol is also typically less than about 5 w/v %, more typically less than about 3 w/v %, even more typically less than about 1.8 w/v % and even more typically less than about 1.2 w/v % of the ophthalmic composition.

Generally, it is contemplated that various amounts of borate can be included in the ophthalmic compositions of the present invention. However, it has been found that lower concentrations of borate, when used in combination with the two or more different polyols, can produce unexpectedly superior antimicrobial activity, preservation efficacy, desired buffering or a combination thereof. Typically, for the present invention, the borate is at least about 0.05 w/v %, more typically at least about 0.1 w/v % and still more typically at least about 0.25 w/v % of the ophthalmic composition. Furthermore, the borate can advantageously be less than about 0.75 w/v %, more typically less than about 0.5 w/v % and still more typically less than about 0.4 w/v %, and even possibly less than about 0.35 w/v % of the ophthalmic composition.

The resistance to normalization of tear pH of the ophthalmic composition within the eye is typically within a desired range. Such resistance can be quantified in terms of the amount or volume of base or acid per amount or volume of ophthalmic composition used to change the composition pH to a predetermined pH. The amount of base or acid required per amount volume of ophthalmic composition to change the natural pH of the composition to the tear pH (7.5) can be significant since it can represent the resistance the composition will provide to normalize to tear pH after the instillation of the composition in the eye. In particular, for the present invention, resistance to normalization to the tear pH can be quantified as the volume of 1 N NaOH (1 normal NaOH) or 1 N HCl (1 normal HCl) required per volume of ophthalmic composition to change the natural pH of the composition to pH of 7.5. For example, the addition of 10 microliters (μl) of 1 N NaOH may move the pH of one milliliter (ml) of the ophthalmic composition from its natural pH (e.g., pH less than 7.0) to a pH of 7.5. The ophthalmic composition of the present invention may not need any NaOH or HCl to achieve pH of 7.5. Typical ophthalmic compositions of the present invention typically need less than 30 μl, more typically less than 25 μl, more typically less than 15 μl, possibly less than 10 μl and even still possibly less than 6.0 μl of 1 N NaOH or 1 N HCl to bring one (1) ml of the ophthalmic composition to a pH of 7.5.

The present invention is particularly directed to the provision of multi-dose ophthalmic compositions that have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

| | Preservative Efficacy Test ("PET") Criteria (Log Order Reduction of Microbial Inoculum Over Time | |
|---|---|---|
| | Bacteria | Fungi |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |

-continued

| | Preservative Efficacy Test ("PET") Criteria (Log Order Reduction of Microbial Inoculum Over Time) | |
|---|---|---|
| | Bacteria | Fungi |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia "A" and "B".

The standards identified above for the USP 27 are substantially identical to the requirements set forth in prior editions of the USP, particularly USP 24, USP 25 and USP 26.

The borate/polyol systems described herein may be included in various types of pharmaceutical compositions to enhance anti-microbial activity and preservation of the compositions, such as ophthalmic, otic, nasal and dermatological compositions, but is particularly useful in ophthalmic compositions. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of ophthalmic compositions, such as ocular lubricating products, artificial tears, astringents, and so on. The compositions may be aqueous or non-aqueous, but will generally be aqueous.

The compositions of the present invention may contain various types of therapeutic agents. The invention can include therapeutic agents that are nonionic. Cationic therapeutic agents may also be utilized in the compositions.

Examples of therapeutic agents that may be contained in the ophthalmic compositions of the present invention include prostaglandin analogs (e.g., latanoprost, travoprost and unoprostone), hypotensive lipids (e.g., bimatoprost), and glucocorticoids (e.g., prednisolone, dexamethasone and lotoporednol), timolol (e.g., timolol maleate), olopatadine (e.g., olopatadine hydrochloride), brinzolamide, dorzolomide, brimonidine (e.g., brimonidine tartrate), emadastine, tandospirone, roscovitine, nepafenac, bradykinin, PDE4 inhibitor, combinations thereof or the like.

The present invention can be directed to the provision of multi-dose ophthalmic compositions in connection with the treatment of conditions wherein the cornea or adjacent ocular tissues are irritated, or conditions requiring frequent application of a composition, such as in the treatment of dry eye patients. The compositions of the present invention can be useful in the field of artificial tears, ocular lubricants, and other compositions used to treat dry eye conditions, as well as other conditions involving ocular inflammation or discomfort. The compositions may also be particularly useful for treating glaucoma.

The compositions of the present invention can include therapeutic agents that exhibit preservative properties. Examples of such therapeutic agent include an anti-infectives and/or anti-biotics. Advantageously, however, the compositions of the present invention exhibit desired preservation without the assistance of therapeutic agents that aid such preservation. Thus, it is contemplated that compositions of the present invention can be entirely or substantially free of any therapeutic agents that exhibit any or any substantial preservative properties. As used herein, substantial preservative properties, as it relates to therapeutic agents, means that the therapeutic agent is at least a portion of the reason that a composition passes one of the U.S. or European preservation efficacy standards discussed below and that, replacement of the therapeutic agent with an equal weight of water, would cause the composition to fail at least one of these standards that it passes with that therapeutic agent. As such, the compositions of the present invention can be free or substantially free of any therapeutic agents that would be considered anti-infectives and/or anti-biotics. In particular, the composition can be free or substantially free of any quinolones, particularly fluoroquinolones.

The compositions of the present invention will generally be formulated as sterile aqueous solutions. The compositions of the present invention are also formulated so as to be compatible with the eye and/or other tissues to be treated with the compositions. The ophthalmic compositions intended for direct application to the eye will be formulated so as to have a pH and tonicity that are compatible with the eye. It is also contemplated that the compositions can be suspensions or other types of solutions.

The compositions will typically have a pH in the range of 4 to 9, preferably 5.5 to 8.5, and most preferably 5.5 to 8.0. Particularly desired pH ranges are 6.0 to 7.8 and more specifically 6.2 to 7.7. The compositions will have an osmolality of 200 to 400 or 450 milliosmoles per kilogram (mOsm/kg), more preferably 240 to 360 mOsm/kg.

The compositions of the present invention may contain various types of pharmaceutical excipients, such as surfactants, viscosity-modifying agents and so on.

The present invention has been found particularly advantageous for forming ophthalmic aqueous suspensions, particularly therapeutic agent suspensions, that include an anionic polymer as a viscosity agent or a suspending agent. Examples of anionic polymers include, without limitation, carboxyvinyl polymer, xanthan gum, gelan gum, sodium carboxymethyl cellulose alginic acid, carageenans. Highly preferred examples of anionic polymers include carboxyvinyl polymer, xanthan gum or a combination thereof. These anionic polymers are typically incompatible with high molecular weight or multi-charged cationic preservatives such as Polyquaternium-1. However, these anionic polymers are substantially more compatible with benzalkonium chloride. Notably, prior to the present invention, relatively high concentrations of benzalkonium chloride were typically needed to preserve anionic polymer based suspensions as well as other ophthalmic compositions to Ph. Eur B or Ph. Eur. A criteria.

Typically, carboxyvinyl polymer will have a network of cross-linked polymer chains. The polymers are often characterized as having carboxylic acid functional groups and preferably contain from 2 to 7 carbon atoms per functional group. Preferred carboxyvinyl polymers include water-soluble and water-swellable carbomers, available under the trade name CARBOPOL from the B.F. Goodrich Company. The commercially available polymers Carbopol 934P, 940 and 974P are highly preferred. The amount of carboxyvinyl polymer present in the pharmaceutical composition of the present invention is typically at least about 0.05%, more typically at least about 0.1% even more typically at least about 0.2%. Moreover, the amount of carboxyvinyl polymer present in the pharmaceutical composition of the present invention is typically less than about 4.0%, more typically less than about 1.2% even more typically less than about 0.7%.

For suspension, particularly those that include carboxyvinyl polymers as a suspending agent, it is desirable for the viscosity of the suspensions to be sufficiently high to keep a therapeutic agent suspended for a substantial period of time. The viscosity of the suspension is typically greater than 5 cps, more typically greater than 20 cps and even more typically greater than 30 cps. The viscosity of the suspension is typically less than 1000 cps, more typically less than 500 cps and even more typically less than 150 cps. The viscosity of the suspension is measured at a high shear rate of 120 sec-1 (e.g. at 60 rpm using spindle CP-52). It is also desirable for such suspension to have osmolality in the range of 240 to 360 mOsm. In one embodiment, sodium chloride is used to adjust the tonicity and viscosity in addition to borate-polyol. When sodium chloride is used, the concentration of sodium chloride is typically high enough to achieve the desired osmolality but less than 0.9%, more typically less than 0.6% and even more typically less than 0.4% since sodium chloride, along with potentially borate and/or mannitol, can negatively impact the viscosity of the suspension for at least some compositions.

When the composition of the present invention is a suspension, it is typically desirable that the therapeutic agent of the suspension be easily redispersed. Suspensions according to the present invention can typically be redispersed with no more than 20 seconds, more typically no more than 15 and even more typically no more than 10 seconds of vigorous shaking.

A surfactant may be used e.g., as a wetting agent in a suspension or as a solubilizer or as a stabilizer. The preferred surfactants are tyloxapol, polysorbate 80 and Polyoxyethylene (POE) (40) Hydrogenated Castor oil (or PEG (40 Hydrogenated castor oil) (HCO-40). When used, the concentration of the surfactant is typically sufficient to achieve a desired degree of wetting by is less than 1.0 wt %, more typically less than 0.5% and even more typically less than 0.1% since higher concentrations of surfactant can negatively effect preservation for at least some compositions.

As an advantage of the present invention, it is believed that the lower concentrations of BAC within the compositions of the present invention allow the compositions to be more suitable for repeated administrations to the eye. There or multiple eye disorders such as elevated intraocular pressure (TOP) for which the desired treatment is repeated administration of the composition of any of the preceding claims to the eye of the mammal repeatedly for an extend period of time. Thus, once the eye[s] of a mammal (e.g., a human) have been diagnosed with such a disorder, chronic treatment of the disorder typically involves repeated administration of a composition to the eye[s]. In such treatment, the composition can be administered at least once a week, more typically at least once a day and even possibly at least twice or three times a day for a period of at least one month, more typically at least six months and even more typically at least one year. The compositions are believed to be quite suitable for such treatment.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Table A below provides a listing of exemplary ingredients suitable for an exemplary preferred formulation of the ophthalmic composition of the present invention and a desired weight/volume percentage for those ingredients.

TABLE A

| Ingredient | w/v percent |
| --- | --- |
| Therapeutic Agent | 0.01, 0.1 or 1.0 |
| Tyloxapol | 0.025 |
| Carbomer | 0.4 or 0.2 |
| Boric Acid | 0.3 |
| Propylene Glycol | 0.75 |
| Mannitol | 0.3 |
| Sodium Chloride | 0.25 |
| BAC | 0.003 |
| NaOH or HCL | sufficient to achieve pH = 6.8 |
| purified water | Q.S. 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

The following examples are presented to further illustrate selected embodiments of the present invention. The formulations shown in the examples were prepared using procedures that are well-known to persons of ordinary skill in the field of ophthalmic pharmaceutical compositions.

Antimicrobial preservative effectiveness as set forth by the examples infra was determined using an organism challenge test according to the methods described in the United States Pharmacopeia 24 (USP) for category 1A products. Samples were inoculated with known levels of one or more of the following: gram-positive vegetative bacteria (*Staphylococcus aureus* ATCC 6538), gram-negative vegetative bacteria (*Pseudomonas aeruginosa* ATCC 9027 and *Escherichia coli* ATCC 8739), yeast (*Candida albicans* ATCC 10231) and mold (*Aspergillus niger* ATCC 16404). The samples were then pulled at specified intervals to determine if the antimicrobial preservative system was capable of killing or inhibiting the propagation of organisms purposely introduced into the formulation. The rate or level of antimicrobial activity determines compliance with the USP preservative efficacy standards for the cited categories of preparations.

TABLE B

Preservative Standards for U.S. Category 1A Products presented as Log Reduction of Organism Population

| Time Pulls | 6 Hours | 24 Hours | 7 days | 14 days | 28 days |
|---|---|---|---|---|---|
| For Bacteria (*S. aureus*, *P. aeruginosa*, and *E. coli*) | | | | | |
| Ph. Eur. A | 2.0 | 3.0 | NA | NA | NR |
| Ph. Eur. B | NA | 1.0 | 3.0 | NI | NI |
| USP | NA | NA | 1.0 | 3.0 | NI |
| For Fungi (*C. albicans* and *A. niger*) | | | | | |
| Ph. Eur. A | NA | NA | 2.0 | NA | NI |
| Ph. Eur. B | NA | NA | NA | 1.0 | NI |
| USP | NA | NA | NI | NI | NI |

NI = No increase at this or any following time pulls
NA = Time point not required for applicable standard (e.g., USP, Ph. Eur. B)
NR = No organisms recovered As shown in Table B, the USP 27 Antimicrobial Effectiveness Test requires that compositions containing Category 1A products have sufficient anti-bacterial activity to reduce an initial inoculum of approximately $10^5$ to $10^6$ bacteria by one log (i.e., a 90% reduction in the microorganism population) over a period of seven (7) days and by three logs (i.e., a 99.9% reduction in the microorganism population) over a period of fourteen (14) days, and requires that there cannot be any increase in the microorganism population following the conclusion of the fourteen day period. Relative to fungi, the USP standards require that the compositions maintain stasis (i.e., no growth) relative to the population of the initial inoculum over the entire 28 day test period. A category 1A product is an injection, or other parenteral including emulsions, otic, sterile nasal products and ophthalmic products made with aqueous bases or vehicles.

The margin of error in calculating microorganism populations is generally accepted to be +/−0.5 logs. Accordingly, the term "stasis", as utilized herein relative to the above-discussed USP standards, means that the initial population cannot increase by more than 0.5 log orders, relative to the initial population.

EXAMPLES

The formulations of Examples A-M are provided as an illustration of desirability of the present invention. The examples illustrate the antimicrobial activity and/or preservative efficacy of the ophthalmic compositions of the present invention containing the combination of two different polyols particularly in combination with the borate, the polymeric quaternary ammonium compound or both. Percentages of ingredients in Examples A-M are weight/volume percents.

Examples A Through C

Table C provides compositions A through C and data related to those formulations. Each of the compositions includes Carbomer 974P for increasing viscosity of the compositions and includes 0.002% BAC, boric acid and two polyols. All three compositions meet Ph. Eur. B/A criteria. These compositions can be used for ophthalmic suspensions of drugs such as brinzolamide, roscovitine, amfenac amide, dexamethasone, bradykinin inhibitor, anecortave acetate, tandospirone, combinations thereof and their combinations with other drugs.

TABLE C

Examples A through C with 0.002% BAC

| Composition | A | B | C |
|---|---|---|---|
| Carbomer 974P | 0.45 | 0.45 | 0.45 |
| Tyloxapol | 0.025 | 0.025 | 0.025 |
| Boric Acid | 0.3 | 0.6 | 0.3 |
| Mannitol | 0.3 | 2.0 | 2 |
| Propylene Glycol | 0.75 | 1 | 0.75 |
| Sodium chloride | 0.3 | None | None |
| Benzalkonium Chloride | 0.002 | 0.002 | 0.002 |
| Disodium Edetate | None | None | None |
| Sodium Hydroxide/HCl | pH 7.0 | pH 7.0 | pH 7.0 |
| Purified Water | QS | QS | QS |
| Osmolality | 279 | 324 | 259 |
| Viscosity (cps) at 120 sec$^{-1}$ | 49.6 | 68.2 | 127.9 |
| Viscosity (cps) at 12 sec$^{-1}$ | 144.4 | 210.4 | 480.7 |

| Microorganisms, Time | | Ph. Eur A Criteria | Ph. Eur B Criteria | Log Reductions | | |
|---|---|---|---|---|---|---|
| *S. aureus* | 6 Hours | 2.0 | — | 4.6 | 4.9 | 2.5 |
| | 24 Hours | 3.0 | 1.0 | 4.9 | 4.9 | 4.9 |
| | 7 Days | | 3.0 | 4.9 | 4.9 | 4.9 |
| | 14 Days | | | 4.9 | 4.9 | 4.9 |
| | 28 Days | NR$^a$ | NI$^b$ | 4.9 | 4.9 | 4.9 |
| *P. aeruginosa* | 6 Hrs | 2.0 | — | 5.0 | 5.0 | 4.8 |
| | 24 Hours | 3.0 | 1.0 | 5.0 | 5.0 | 4.8 |
| | 7 Days | | 3.0 | 5.0 | 5.0 | 4.8 |
| | 14 Days | | | 5.0 | 5.0 | 4.8 |
| | 28 Days | NR | NI | 5.0 | 5.0 | 4.8 |

TABLE C-continued

| \multicolumn{6}{c}{Examples A through C with 0.002% BAC} | | | | | |
|---|---|---|---|---|---|
| E. coli[c] | 6 Hours | NA[d] | NA | 5.0 | 5.0 | 3.0 |
| | 24 Hours | | | 5.0 | 5.0 | 5.0 |
| | 7 Days | | | 5.0 | 5.0 | 5.0 |
| | 14 Days | | | 5.0 | 5.0 | 5.0 |
| | 28 Days | | | 5.0 | 5.0 | 5.0 |
| C. albicans | 7 Days | 2.0 | — | 4.7 | 4.7 | 4.8 |
| | 14 Days | NI | 1.0 | 4.7 | 4.7 | 4.8 |
| | 28 Days | NI | NI | 4.7 | 4.7 | 4.8 |
| A. niger | 7 Days | 2.0 | — | 3.1 | 3.1 | 3.7 |
| | 14 Days | NI | 1.0 | 3.6 | 4.2 | 4.3 |
| | 28 Days | NI | NI | 5.2 | 5.2 | 5.1 |

[a]NR = No recovery
[b]NI = No increase
[c]The Ph. Eur. has no requirements for E. coli
[d]NA = Not Applicable

Example D

Example D presented in Table 3 is a composition with 0.002% BAC, boric acid and two different polyols and is projected to meet Ph. Eur B and A PET criteria.

TABLE D

| Example D with 0.002% BAC | |
|---|---|
| Composition | D |
| Boric Acid | 0.3 |
| Sorbitol | 0.25 |
| Propylene Glycol | 1.6 |
| Benzalkonium Chloride | 0.002 |
| Sodium Hydroxide and/or Hydrochloric Acid | Adjust pH 6.0 ± 0.2 |
| Purified Water | QS 100 w/v% |
| Microorganisms | Log Reductions |
| Staph A. | 6 Hr/24 Hr/7Day | 4.9/4.9/4.9 |
| Pseudomonas A. | 6 Hr/24 Hr/7Day | 5.0/5.0/5.0 |

TABLE D-continued

| Example D with 0.002% BAC | | |
|---|---|---|
| E. Coli | 6 Hr/24 Hr/7Day | 5.0/5.0/5.0 |
| Candida A. | 7 Day | 5.0 |
| A. Niger | 7 Day | 3.7 |
| | | Projected to pass, Ph. Eur. B and Ph. Eur A Criteria |

Examples E-G

All three examples E-G contain 0.001% BAC, boric acid. Example E also includes two different polyols, sorbitol and propylene glycol. It is projected to pass Ph. Eur B and A PET criteria. However examples F which does not contain boric acid and example G which contains only one polyol (sorbitol) with boric acid fail Ph. Eur B & Ph. Eur A criteria.

TABLE E

| Examples E to G with 0.001% BAC | | | |
|---|---|---|---|
| Composition | E | F | G |
| Olopatadine Hydrochloride | 0.333% | 0.333% | 0.333% |
| Povidone K29-32 | 1.8% | 1.8% | 1.8% |
| Caffeine, anhydrous | 1% | 1% | 1% |
| Sorbitol | 0.25% | None | 0.25% |
| Propylene Glycol | 0.75 | None | None |
| Sodium Chloride | None | 0.5 | 0.3 |
| Benzalkonium Chloride | 0.001% | 0.001% | 0.001% |
| Boric Acid | 0.6% | None | 0.6% |
| Sodium Hydroxide and/or Hydrochloric Acid | Adjust pH to 7.0 | Adjust pH to 7.0 | Adjust pH to 7.0 |
| Dibasic Sodium Phosphate Anhydrous | None | 0.42 | None |
| Purified Water | QS to 100% | QS to 100% | QS to 100% |
| Microorganisms | \multicolumn{3}{c}{Log Reductions} | | |
| 6 Hr/24 Hr/7D Staph A. | 4.3/4.9/4.9 | 0.3/3.1/4.9 | 0.6/4.4/4.9 |
| 6 Hr/24 Hr/7D Pseudomonas A. | 4.9/4.9/4.9 | 3.9/4.9/4.9 | 4.9/4.9/4.9 |
| 6 Hr/24 Hr/7D Hr. E. Coli | 2.3/4.9/4.9 | 2.4/3.8/4.9 | 0.2/0.9/4.9 |
| 7 D Candida A. | 5.0 | 3.1 | 5.0 |
| 7 D/14D/28D A. Niger | 2.0 | 0.5 | 1.4 |
| | Projected to Pass Ph. Eur. B and A | Fail Ph. Eur. B and A | Fail Ph. Eur. B and A |

Examples H-M

Each of examples H-M meet Ph. Eur A and/or Ph. Eur B. preservation efficacy.

TABLE F

Compositions H-J with carboxyvinyl polymer and 0.001% BAC
Each of compositions H-J, amongst other uses, can be used as suspension vehicles for suspending therapeutic agents.

| Composition | | H | I | J |
|---|---|---|---|---|
| Carbomer 974P | | 0.45 | 0.45 | 0.45 |
| Tyloxapol | | 0.025 | 0.025 | 0.025 |
| Boric Acid | | 0.3 | 0.3 | 0.6 |
| Mannitol | | 1.5 | 0.3 | 2.0 |
| Propylene Glycol | | 0.75 | 0.75 | 0.75 |
| Sodium chloride | | 0.15 | 0.3 | None |
| Benzalkonium Chloride | | 0.001 | 0.001 | 0.001 |
| Sodium Hydroxide/HCl | | pH 7.0 | pH 7.0 | pH 7.0 |
| Purified Water | | QS | QS | QS |
| Osmolality | | 278 | 274 | 278 |
| Viscosity (cps) at 120 $sec^{-1}$ | | 63.1 | 53.8 | 59.1 |
| Viscosity (cps) at 12 $sec^{-1}$ | | 169 | 149 | 172 |
| S. aureus | 6 Hours | 0.2 | 0.0 | 0.2 |
| | 24 Hours | 2.6 | 1.4 | 3.0 |
| | 7 Days | 5.0 | 5.0 | 5.0 |
| | 14 Days | 5.0 | 5.0 | 5.0 |
| | 28 Days | 5.0 | 5.0 | 5.0 |
| P. aeruginosa | 6 Hrs | 4.9 | 4.9 | 4.9 |
| | 24 Hours | 4.9 | 4.9 | 4.9 |
| | 7 Days | 4.9 | 4.9 | 4.9 |
| | 14 Days | 4.9 | 4.9 | 4.9 |
| | 28 Days | 4.9 | 4.9 | 4.9 |
| E. coli | 6 Hours | 1.4 | 1.4 | 3.1 |
| | 24 Hours | 3.1 | 3.4 | 5.0 |
| | 7 Days | 5.0 | 5.0 | 5.0 |
| | 14 Days | 5.0 | 5.0 | 5.0 |
| | 28 Days | 5.0 | 5.0 | 5.0 |
| C. albicans | 7 Days | 3.0 | 3.5 | 4.8 |
| | 14 Days | 4.3 | 4.8 | 4.8 |
| | 28 Days | 4.8 | 4.8 | 4.8 |
| A. niger | 7 Days | 3.2 | 3.5 | 3.6 |
| | 14 Days | 3.7 | 3.4 | 3.5 |
| | 28 Days | 3.6 | 3.0 | 3.4 |

TABLE G

Roscovitine formulations with low BAC, boric acid and two polyols

| Composition | | K |
|---|---|---|
| Roscovitine (AL-39256) | | 1 |
| Carbomer 974P | | 0.45 |
| Tyloxapol | | 0.025 |
| Boric Acid | | 0.3 |
| Mannitol | | 0.3 |
| Propylene Glycol | | 0.75 |
| Sodium chloride | | 0.28 |
| Benzalkonium Chloride | | 0.003 |
| Sodium Hydroxide/HCl | | pH 7.2 |
| Purified Water | | QS |
| Osmolality (mOsm/kg) | | 271 |
| Viscosity (cps) at 12 $sec^{-1}$ | | 198.1 |
| Viscosity (cps) at 120 $sec^{-1}$ | | 66.5 |
| S. aureus | 6 Hours | 5.1 |
| | 24 Hours | 5.1 |
| | 7 Days | 5.1 |
| | 14 Days | 5.1 |
| | 28 Days | 5.1 |
| P. aeruginosa | 6 Hrs | 4.9 |
| | 24 Hours | 4.9 |
| | 7 Days | 4.9 |
| | 14 Days | 4.9 |
| | 28 Days | 4.9 |
| E. coli$^c$ | 6 Hours | 4.9 |
| | 24 Hours | 4.9 |
| | 7 Days | 4.9 |
| | 14 Days | 4.9 |
| | 28 Days | 4.9 |
| C. albicans | 7 Days | 4.8 |
| | 14 Days | 4.8 |
| | 28 Days | 4.8 |
| A. niger | 7 Days | 5.1 |
| | 14 Days | 5.1 |
| | 28 Days | 5.1 |

Composition K exhibits a resistance to tear normalization of about 4.4.

TABLE H

Brinzolamide and Brinzolamide/Brimonidine formulations with low BAC, boric acid and two polyols

| Composition | M | N |
|---|---|---|
| Brinzolamide | 1.0 | 1.0 |
| Brimonidine | 0.15 | 0.15 |

TABLE H-continued

Brinzolamide and Brinzolamide/Brimonidine formulations with low BAC, boric acid and two polyols

| Composition | | M | N |
|---|---|---|---|
| Carbopol 974P | | 0.4 | 0.4 |
| Tyloxapol | | 0.025 | 0.025 |
| Boric Acid | | 0.3 | 0.3 |
| Mannitol | | 0.3 | 0.3 |
| Propylene Glycol | | 0.75 | 0.75 |
| Sodium Chloride | | 0.23 | 0.23 |
| Benzalkonium Chloride | | 0.003 | 0.003 |
| Sodium Hydroxide, and/or Hydrochloric Acid | | QS to pH 6.5 ± 0.2 | QS to pH 6.5 ± 0.2 |
| Purified Water | | QS to 100% | QS to 100% |
| S. aureus | 6 Hours | 5.0 | 5.0 |
| | 24 Hours | 5.0 | 5.0 |
| | 7 Days | 5.0 | 5.0 |
| | 14 Days | 5.0 | 5.0 |
| | 28 Days | 5.0 | 5.0 |
| P. aeruginosa | 6 Hrs | 5.0 | 5.0 |
| | 24 Hours | 5.0 | 5.0 |
| | 7 Days | 5.0 | 5.0 |
| | 14 Days | 5.0 | 5.0 |
| | 28 Days | 5.0 | 5.0 |
| E. coli$^c$ | 6 Hours | 5.0 | 5.0 |
| | 24 Hours | 5.0 | 5.0 |
| | 7 Days | 5.0 | 5.0 |
| | 14 Days | 5.0 | 5.0 |
| | 28 Days | 5.0 | 5.0 |
| C. albicans | 7 Days | 4.8 | 4.8 |
| | 14 Days | 4.8 | 4.8 |
| | 28 Days | 4.8 | 4.8 |
| A. niger | 7 Days | 4.3 | 4.4 |
| | 14 Days | 4.1 | 4.3 |
| | 28 Days | 4.2 | 4.1 |

Compositions M and N exhibit a resistance to tear normalization of about 18.

TABLE I

Example O through V

| Composition | O | P | Q | R |
|---|---|---|---|---|
| Carbopol 974P | 0.4 | 0.4 | 0.4 | 0.4 |
| Tyloxapol | 0.025 | 0.025 | 0.025 | 0.025 |
| Boric Acid | 0.3 | 0.3 | None | None |
| Mannitol | 0.3 | 0.3 | 0.3 | 0.3 |
| Propylene Glycol | 0.75 | 0.75 | 0.75 | 0.75 |
| Sodium Chloride | 0.23 | 0.23 | 0.23 | 0.40 |
| Benzalkonium Chloride | 0.002 | None | 0.002 | 0.002 |
| Sodium Hydroxide, and/or Hydrochloric Acid | QS to pH 6.5 ± 0.2 | QS to pH 6.5 ± 0.2 | QS to pH 6.5 ± 0.2 | QS to pH 6.5 ± 0.2 |
| Purified Water | QS to 100% | QS to 100% | QS to 100% | QS to 100% |
| Osmolality (mOsm/kg) | 253 | 244 | 200 | 268 |
| Viscosity (cps) at 120 sec$^{-1}$ | 51 | 59 | 63 | 21 |

| Composition | S | T | U | V |
|---|---|---|---|---|
| Carbopol 974P | 0.4 | 0.4 | 0.4 | 0.4 |
| Tyloxapol | 0.025 | 0.025 | 0.025 | 0.025 |
| Boric Acid | 0.3 | 0.3 | 0.3 | 0.3 |
| Mannitol | None | 0.3 | 0.3 | 0.3 |
| Propylene Glycol | 0.75 | None | None | 0.75 |
| Sodium Chloride | 0.23 | 0.23 | 0.53 | None |
| Benzalkonium Chloride | 0.002 | 0.002 | 0.002 | 0.002 |
| Sodium Hydroxide, and/or Hydrochloric Acid | QS to pH 6.5 ± 0.2 | QS to pH 6.5 ± 0.2 | QS to pH 6.5 ± 0.2 | QS to pH 6.5 ± 0.2 |
| Purified Water | QS to 100% | QS to 100% | QS to 100% | QS to 100% |
| Osmolality (mOsm/kg) | 237 | 149 | 240 | 179 |
| Viscosity (cps) at 120 sec$^{-1}$ | 59 | 53 | 15 | >155 |

Examples O to V show that both osmolality and viscosity of Carbomer containing compositions can be obtained in the desired range by using sodium chloride while keeping sodium concentration lower than 0.4%.

We claim:

1. A multi-dose ophthalmic composition, comprising:
   a first polyol, the first polyol being selected from mannitol, sorbitol or a combination thereof;
   a second polyol, the second polyol being selected from propylene glycol, glycerine or a combination thereof;
   an effective amount of borate, the effective amount being less than about 0.5 w/v % of the overall composition;
   BAC as an anti-microbial preservative, the concentration of BAC in the composition being greater than 0.00001 w/v % but less than 0.0035 w/v %;
   a therapeutic agent; and
   water;
   wherein the composition is a suspension with the therapeutic agent and carboxyvinyl polymer as a suspending agent.

2. A composition as in claim 1 wherein the composition satisfies Ph. Eur. A, Ph. Eur. B or both.

3. A composition as in claim 1 wherein the concentration of the first polyol is at least 0.01 w/v % but is less than about 0.35 w/v %.

4. A composition as in claim 1 wherein concentration of the BAC is less than 0.0025 w/v % of the composition.

5. A composition as in claim 1 wherein concentration of the BAC is less than 0.0015 w/v % of the composition.

6. A composition as in claim 1 wherein the first polyol is mannitol and the second polyol is propylene glycol.

7. A composition as in claim 1 wherein the composition is substantially free of any preservatives other than benzalkonium chloride.

8. A composition as in claim 1 wherein the resistance provided by the composition to normalization of tear pH after instillation in the eye is less than 25 µl of 1 M NaOH/mL of composition.

9. A composition as in claim 1 wherein the pH of the composition is from about 6.2 to about 7.7.

10. A composition as in claim 1 wherein the therapeutic agent is brinzolamide.

11. A composition as in claim 1 wherein the composition is free of any quinolone anti-infective or anti-biotic therapeutic agent.

12. A composition as in claim 1 wherein the suspension is redispersed with no more than 15 seconds of vigorous shaking.

13. A multi-dose ophthalmic composition, comprising:
a first polyol, the first polyol being selected from mannitol, sorbitol or a combination thereof and wherein the concentration of the first polyol is at least 0.01 w/v % but no greater than 0.5 w/v %;
a second polyol, the second polyol being selected from propylene glycol, glycerine or a combination thereof wherein the second polyol is at least about 0.1 but less than about 5 w/v % of the composition;
an effective amount of borate, the effective amount being less than about 0.5 w/v % of the overall composition;
therapeutic agent;
BAC as an anti-microbial preservative, the concentration of BAC in the composition being greater than 0.00001 w/v % but less than 0.0035 w/v %; and
water;
wherein the composition is substantially free of any preservatives other than benzalkonium chloride and wherein the composition is a suspension with the therapeutic agent and carboxyvinyl polymer as a suspending agent.

14. A composition as in claim 13 wherein the resistance provided by the composition to normalization of tear pH after instillation in the eye is less than 15 µl of 1 M NaOH/mL of composition.

15. A composition as in claim 13 wherein the viscosity of the suspension is greater than 20 cps but less than 500 cps with the viscosity of the suspension being measured at a high shear rate of 120 sec-1 at room temperature.

16. A composition as in claim 15 wherein the suspension is redispersed with no more than 15 seconds of vigorous shaking.

17. A composition as in claim 13 wherein the composition is free of any quinolone anti-infective or anti-biotic therapeutic agent.

18. A composition as in claim 13 wherein the composition is configured for administration to the eye of the mammal repeatedly for an extend period of time of and is administered at least once a week and wherein the eye of the mammal has been diagnosed with an eye disorder that is suitably treated with chronic administration of the therapeutic agent.

19. A composition as in claim 18 wherein the eye disorder is elevated intraocular pressure.

20. A multi-dose ophthalmic composition, comprising:
mannitol wherein the concentration of the mannitol is at least 0.01 w/v % but no greater than 0.5 w/v %;
propylene glycol wherein the concentration of the mannitol is at least 0.01 w/v % but no greater than 0.5 w/v %;
an effective amount of borate, the effective amount being less than about 0.5 w/v % of the overall composition;
therapeutic agent selected from brinzolamide, brimonidine or a combination thereof;
carboxyvinyl polymer that is at least about 0.1 w/v % but less than about 1.2 w/v % of the composition;
BAC as an anti-microbial preservative, the concentration of BAC in the composition being greater than 0.00001 w/v % but less than 0.0035 w/v %; and
water;
wherein:
i. the composition is substantially free of any preservatives other than benzalkonium chloride;
ii. the resistance provided by the composition to normalization of tear pH after instillation in the eye is less than 15 µl of 1 M NaOH/mL of composition;
iii. the composition is a suspension with the brinzolamide and carboxyvinyl polymer as a suspending agent;
iv. the viscosity of the suspension is greater than 20 cps but less than 500 with the viscosity of the suspension being measured at a high shear rate of 120 sec-1 at room temperature;
v. the composition is free of any quinolone anti-infective or anti-biotic therapeutic agent; and
vi. the pH of the composition is from about 6.2 to about 7.7.

* * * * *